United States Patent [19]

Drusiani

[11] Patent Number: 5,088,198
[45] Date of Patent: Feb. 18, 1992

[54] DEVICE FOR THE DISINFECTION OF PRUNED BRANCHES OR VINE-SHOOTS, APPLIED OR APPLICABLE TO PNEUMATIC SHEARS

[75] Inventor: Franco Drusiani, Savena, Italy
[73] Assignee: M.A.I.Bo S.R.L., Bologna, Italy
[21] Appl. No.: 605,755
[22] Filed: Oct. 30, 1990

[30] Foreign Application Priority Data

Aug. 3, 1990 [IT] Italy ................. 3633A/90

[51] Int. Cl.⁵ ............................ B25F 3/00
[52] U.S. Cl. ............................. 30/123.3
[58] Field of Search .......... 30/123.3; 83/169

[56] References Cited

U.S. PATENT DOCUMENTS

| | | | |
|---|---|---|---|
| 2,747,330 | 5/1956 | Simpkins | 30/123.3 |
| 2,870,573 | 1/1959 | Scadden | 30/123.3 |
| 4,219,963 | 9/1980 | Mullet | 30/123.3 |

FOREIGN PATENT DOCUMENTS 616057  6/1961  Italy ................. 30/123.3

*Primary Examiner*—Frank T. Yost
*Assistant Examiner*—Paul M. Heyrana, Sr.
*Attorney, Agent, or Firm*—Darby & Darby

[57] ABSTRACT

A system for the disinfection of prune branches or vines shoots includes a pair of shears having blades hinged by a pin. A specially shaped thin blade is fastened to the pin for holding a nozzle located on the cutting edge of the cutting blades. Disinfectant liquid is contained under pressure in a tank and is delivered to the nozzle through a valve attached to the body of the shears and actuated by a lever that also controls operation of the shear blades. Pressurized liquid disinfectant is delivered concurrently with the shearing action of the blades. All components for disinfectant delivery are external to the shear body and blades and detachable therefrom.

7 Claims, 1 Drawing Sheet

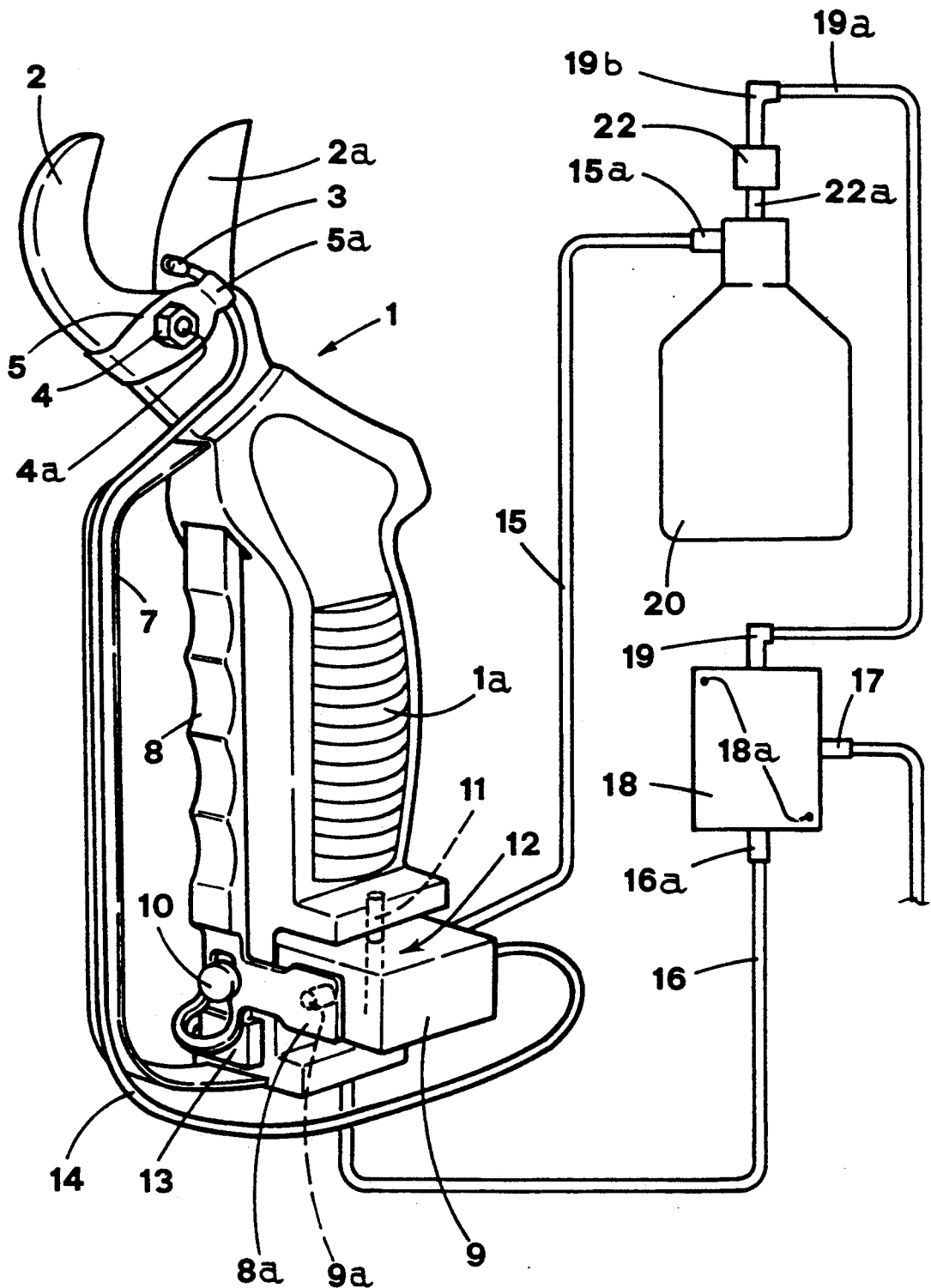

DEVICE FOR THE DISINFECTION OF PRUNED BRANCHES OR VINE-SHOOTS, APPLIED OR APPLICABLE TO PNEUMATIC SHEARS

BACKGROUND OF THE INVENTION

This invention concerns the technical field of plant pruning, particularly of vines, carried out by means of mechanical devices.

DESCRIPTION OF THE PRIOR ART

It is known that when plants, e.g. vines, are pruned, the part of the branch or shoot remaining attached to the plant may be more easily attacked by infecting agents (e.g. pests).

Therefore, the whole plant, having many of its branches or shoots chopped off during pruning, gets "ill", with obvious negative effects on the production which can be obtained from the plant, both in terms of quantity and of quality; the latter, in particular, may turn out to be absolutely unacceptable when a plant disease makes the fruits no longer eatable, or not hygienically guaranteed.

In order to eliminate such drawbacks, the usual practice involves the systematic disinfection of every single branch or vine-shoot left attached to the plant, by operating manually with a brush dipped in a special disinfecting solution.

It is easily understandable how such an operation may turn out to be particularly expensive in terms of labour as well as of time required to be carried out.

A known solution to solve such problems involves the use of air under pressure mixed with a disinfecting solution to operate the shears.

The mixing of air and disinfectant is carried out upstream of the shears, by means of a device taking the disinfectant from a special external tank.

When the air under pressure is discharged, after a branch has been pruned, the air is atomized, together with the disinfectant mixed, on the cut-off area.

In this way, however, the disinfectant mixed with air inside the shears in the long run carries out a corroding action on the pneumatic system inside the shears.

This brings about serious drawbacks, since at least a careful and frequent servicing is required, which, anyway, cannot cope with said corroding action in the long run, with a consequent reduction of the "life" of the shears.

Furthermore, said solution brings about the need of a pair of shears for pruning and simultaneous disinfection specially made for the purpose. From the beginning, such a very specific tool relative to the field of application, has not been very versatile.

SUMMARY OF THE INVENTION

The object of the invention is to provide a device for the disinfection of pruned branches or vine-shoots applied or applicable to pneumatic shears, which allows performance of an effective disinfecting action with a substantial saving in terms of time and labour, as well as obtaining a higher functionality, a higher reliability and a better versatility of use as compared to the known model of shears mentioned above.

The invention presented provides for applying, to pneumatic shears of a known type, a device comprising: a valve fastened externally to the lower part of the shears and operated through the actuating means of the shears; a nozzle associated with said shears and turned towards the cutting edge of the blades; means for supporting said nozzle, removably fastened to the shears; a plurality of tubes for connecting the valve with the nozzle, the valve with a tank containing the disinfectant, a distributor of air under pressure with the shears and with a pressure regulator, located above the tank.

BRIEF DESCRIPTION OF THE DRAWINGS

The features of the invention not apparent from the above description are pointed out here below, with reference to the drawing enclosed herewith, where:

The Figure shows an assembly view of the whole device presented hereby.

DESCRIPTION OF THE PREFERRED EMBODIMENT

With reference to said figure, pneumatic shears 1 of a known type, include a handle 1a to which two blades 2 and 2a are restrained, hinged to each other through a pin 4a locked by a corresponding nut 4.

To the handle 1a of the shears, a lever 8 is hinged for actuating the shears pneumatic control device, which acts on the control device through a small piston 10, subjected to the action of a spring not illustrated.

Furthermore, the small piston 10 causes the return of the handle to the rest position once the pressure, exerted manually on the lever 8 by the operator, has ceased, when the shears are operated, thanks to the reaction of the spring.

To the lower part of the lever, an actuating means 8a is fastened, e.g. an appendix, extending sidewise in the lower part of the lever 8, so that it may act on a small pin 9a for operating a valve 9, removably fastened to the shears 1 into a corresponding seat 12, provided on the shears, e.g. by means of a screw 11.

A protecting element 7, or handguard, extends along the handle 1a, "covering" the lever 8.

The valve 9, on the side opposite to the small pin 9a, has two unions, not illustrated, for air inlet and outlet. From the outlet union of the valve, a first duct 14 branches off, e.g. a tube section ending with a spraying means 3, e.g. a nozzle, located on one of the blades, in proximity of its cutting edge.

To the inlet union of the valve 9, a second duct 15 is connected, e.g. a tube, leading to a corresponding mouthpiece 15a of a tank 20 containing a disinfectant liquid.

The nozzle may be placed either on the right or on the left side of the blades, according to where the part of the branch just pruned, that is, remaining attached to the plant, usually finds itself.

As a matter of fact, when the operator is left-handed, the nozzle shall be located on the blade opposite to that where the nozzle is placed if the operator is right-handed.

The nozzle is held in a suitable position by a holding means 5, e.g. a thin plate, removably fastened to said pin 4a through the same nut 4 locking the latter.

Said thin plate has an oblong shape, with an end edge 5a bent to be complementary to the profile of the nozzle 3 to lock the nozzle removably in its place.

The tank 20 is provided with two unions 22a and 15a, respectively for connection with a pressure regulator 22 and, through the tube 15, with the valve 9.

Furthermore, from the pressure regulator 22 a union 19b branches off, for connecting a third duct 19a, e.g. a tube, through which air under pressure is conveyed from a distributor 18 by means of a union 19 connecting the tube 19a with the distributor 18. The latter is also provided both with a union 17, for connection with a common air supply source, and with a union 16, for feeding air to the shears 1, connected with the distributor 18 by means of a fourth duct 16, e.g. a tube.

From the drawing it is possible to notice the presence, in the lower part of the shears 1, of a small lever 13 of a known type, which is sliding to allow or prevent the operation by means of the lever 8 of the same shears.

The tank 20 and the distributor 18 are contained in a small knapsack, not illustrated, with said distributor fastened to one of the belts of said knapsack by means of small bolts 18a.

On the other hand, the shears 1 are contained in a special holster-type case applied to the operator's leg.

In order to increase the functional capacity of the shears improved in accordance with the invention presented hereby, the tubes 16 and 15 for feeding air to the shears and disinfectant to the nozzle 3, may be enclosed in one single sheath.

The operation of the device is very simple: after connecting the union 17 with a common air supply source, by acting on the lever 8 to operate the shears, with the movement of the blades 2 and 2a to chop off the branch or vine-shoot to be pruned, also the valve 9 is actuated.

In this way, the disinfectant liquid is forced by the air under pressure contained in the tank 20 through the tube 15 into the valve 9.

Being ejected from the latter, the disinfectant goes through the tube 14 and it is sprayed by the nozzle 3 so to disinfect the section of pruned branch remaining attached to the plant; all this happens in a proper phase relation.

When the lever 8 is released, the lever is brought back to the rest position by the reaction of the small piston 10.

In this way, both the control device of the shears 1 and the device for disinfection presented hereby are stopped at the same time.

As a matter of fact, the release of the lever 8 with the appendix 8a associated thereto, causes the closing of the valve 9 and, as a consequence, the stopping of the flow of disinfectant coming out of the nozzle 3.

The obvious advantages, already mentioned above, consist in the possibility of coping with all the drawbacks related to the use and servicing of the conventional systems for disinfection, either manual or mechanized, with a reduction of costs both in terms of labour and of time required for carrying out the disinfection.

Furthermore, the best accessibility to every single part of the device proposed hereby is evident, and makes any servicing extremely simple.

In particular, the inside of the shears is not affected in any way by liquids which could be corrosive or could damage it somehow.

By the invention presented hereby, all the drawbacks mentioned above and typical of the known art are completely eliminated; in fact, the shears so obtained turn out to be extremely versatile, and usable both with and without the device for disinfection according to the invention presented hereby.

A further feature of the invention presented hereby is that it provides the possibility of supplying either the shears complete with the device for disinfection presented hereby, however removable at any moment, or the above-mentioned device alone in an assembly kit.

This solution, for instance, may be preferred by a customer who already owns "simple" pneumatic shears.

It is understood that the above has been described by way of example and not as a limitation, therefore any possible variations of technical-practical nature are understood as covered by the technical solution described above and claimed here below.

What is claimed is:

1. A pneumatic pruning shear system for disinfection of pruned branches or vine-shoots, comprising:
   a shear body and blades, each blade having a cutting edge, said blades being hinged to each other by means of a pin, said body including a seat;
   at least one pneumatic valve removably fastened in said seat to said body, each said at least one valve having an inlet and an outlet;
   actuating means connected to said body for causing said at least one valve to open and close, when actuated;
   spraying means removably located near the cutting edge of one said blade, said spraying means including an outlet nozzle directed toward the cut surface of a branch or shoot remaining on the pruned plant after a cutting operation;
   locking means for removably fastening said spraying means to said blade of said shears;
   a first duct connected between an outlet of said at least one valve and said spraying means;
   at least one tank for containing a disinfectant liquid;
   a second duct connected between said at least one tank and the inlet of said at least one valve, opening said at least one valve by said actuating means connecting said first duct to said second duct for flow therethrough;
   an air distributor for connection to a source of air under pressure, said distributor having at least one air outlet;
   a third duct connected between said at least one air outlet and said at least one tank to pressurize said disinfectant liquid;
   a fourth duct connected between said at least one air outlet to said at least one valve, opening said valve by said actuating means connecting the pressurized air of said fourth duct to said shears to operate said blades, liquid disinfectant being sprayed concurrently with closing of said blades.

2. A system as in claim 1, wherein said actuating means include an appendix integral with a lever for controlling said shears, said appendix being positioned to act on a small pin of said valve, thus causing said valve opening, the passage through said valve of disinfectant liquid coming from said tank and being directed to said disinfectant spraying means through said first duct and second duct.

3. A system as in claim 1, wherein said spraying means includes a nozzle, said locking means including a thin plate having at least one edge bent to be complementary to the profile of said nozzle.

4. A system as in claim 3, wherein said thin plate is removably fastened to said shears by means of said pin and a locking nut connected to said pin.

5. A system as in claim 1, wherein said first duct, second duct, third duct and fourth duct are tubes external to the shears.

6. A system as in claim 5, wherein said shears include a protection element and said first duct is a tube fastened externally to said shears and extending along said protection element of said shears, to connect said valve with said spraying means.

7. A system as in claim 1, wherein said at least one valve and said spraying means are external to said shears.

* * * * *